United States Patent
Abe et al.

(10) Patent No.: US 6,189,460 B1
(45) Date of Patent: Feb. 20, 2001

(54) COMBUSTION SYSTEM FOR SOOTY SMOKE GENERATING FACILITIES

(75) Inventors: Yoshiharu Abe; Yoshiyasu Fukui; Noriyuki Yamada; Takanori Shiina; Setsuo Kikuchi; Yoshinori Akagawa, all of Wako (JP)

(73) Assignee: Honda Giken Kogyo Kabushiki Kaisha, Tokyo (JP)

( * ) Notice: Under 35 U.S.C. 154(b), the term of this patent shall be extended for 0 days.

(21) Appl. No.: 08/999,021

(22) Filed: Dec. 29, 1997

(30) Foreign Application Priority Data

Dec. 30, 1996 (JP) .................................................. 8-359188
Feb. 20, 1997 (JP) .................................................. 9-051170

(51) Int. Cl.$^7$ ...................................................... F23N 5/00
(52) U.S. Cl. .......................... 110/185; 110/191; 110/345; 110/186; 431/4; 431/76
(58) Field of Search ..................................... 110/185, 186, 110/187, 188, 189, 190, 191, 342, 344, 345, 343, 203, 215, 216, 192, 193; 431/18, 75, 76, 2, 4; 236/15 R, 15 BA, 15 BB, 15 BD, 15 E (56) References Cited

U.S. PATENT DOCUMENTS

| 4,793,268 | * | 12/1988 | Kukin et al. | 236/15 E X |
|---|---|---|---|---|
| 5,103,742 | * | 4/1992 | Valentino | 110/185 X |
| 5,123,363 | * | 6/1992 | Martin | 110/345 |

(List continued on next page.)

FOREIGN PATENT DOCUMENTS

| 58-061181 | 4/1983 | (JP) . |
|---|---|---|
| 01014515 | 1/1989 | (JP) . |
| 04161849 | 6/1992 | (JP) . |
| 05312796 | 11/1993 | (JP) . |
| 06066417 | 3/1994 | (JP) . |
| 07265661 | 10/1995 | (JP) . |
| 08110027 | 4/1996 | (JP) . |
| 08200658 | 8/1996 | (JP) . |
| 08266863 | 10/1996 | (JP) . |
| 09033026 | 2/1997 | (JP) . |

* cited by examiner

Primary Examiner—Ira S. Lazarus
Assistant Examiner—Ljiljana V. Ciric
(74) Attorney, Agent, or Firm—Arent Fox Kintner Plotkin & Kahn (57) ABSTRACT

A combustion system for reducing an amount of air polluting substances in a combustion exhaust gas produced in a combustion furnace comprises a combustion furnace configured to produce a combustion exhaust gas upon combustion of a combustible material, wherein the combustion exhaust gas contains an amount of air polluting substances; an analyzer suitable for analyzing the combustion exhaust gas and producing an analytical signal; a conduit suitable for conducting the combustion exhaust gas from the outlet opening to the analyzer, wherein the conduit is located adjacent the outlet opening of the combustion furnace; a controller suitable for processing the analytical signal produced by the analyzer and outputting a first control signal and a second control signal, based on the analytical signal; a neutralizer supplier suitable for supplying the combustion furnace with an amount of neutralizers to reduce the amount of air polluting substances in the combustion exhaust gas, wherein the amount of neutralizers supplied to the combustion furnace is based on the first control signal outputted by the controller; and an operating condition readjuster suitable for readjusting at least one operating condition of the combustion furnace selected from the group consisting of (1) a temperature of the combustion furnace, (2) a time for combusting the combustible material, and (3) an air flow in the combustible furnace, to reduce the amount of air polluting substances in the combustion exhaust gas, wherein the at least one operating condition is readjusted based on the second control signal outputted by the controller.

27 Claims, 7 Drawing Sheets

U.S. PATENT DOCUMENTS

| | | | | |
|---|---|---|---|---|
| 5,233,934 | * | 8/1993 | Krigmont et al. | 110/345 |
| 5,251,564 | * | 10/1993 | Rim et al. | 110/345 X |
| 5,336,081 | * | 8/1994 | Saito et al. | 110/342 X |
| 5,425,916 | * | 6/1995 | Beer et al. | 431/18 X |
| 5,524,557 | * | 6/1996 | Spokoyny | 110/203 |
| 5,676,071 | * | 10/1997 | Horler et al. | 110/343 |
| 5,678,493 | * | 10/1997 | Kelley et al. | 110/185 |
| 5,681,375 | * | 10/1997 | West, II et al. | 110/345 X |
| 5,832,842 | * | 11/1998 | Frontini et al. | 110/190 |

COMBUSTION SYSTEM FOR SOOTY SMOKE GENERATING FACILITIES

BACKGROUND OF THE INVENTION

1. Field of the Invention

This invention relates to a combustion system used in sooty smoke generating facilities such as a boiler equipment or a combustion furnace and more particularly to such combustion system provided with control means adapted to control the combustion system so that air polluting substances otherwise contained in exhaust gas generated from the boiler equipment or otherwise contained in exhaust gas generated from the combustion furnace usually used for incineration of general garbage or industrial waste may be effectively collected before emission into the atmosphere, and monitoring means adapted to detect an efficiency deterioration possibly occurring in a dust collector which functions, in turn, to catch and collect sooty dust contained in the exhaust gas from the combustion furnace.

2. Description of the Related Art

Exhaust gas generated from the facilities such as the boiler equipment and the combustion furnace contains sooty dust and the other various air polluting substances. Particularly the exhaust gas generated from urban garbage incinerators contains, in addition to carbon dioxide, water vapor and oxygen, various specified substances under the regulations such as soot and dust, hydrogen chloride (HCl), sulfur oxides ($SO_x$) and nitrogen oxides ($NO_x$). These substances are legally regulated, for example, by the Japanese Air Pollution Control Act with respect to its factors such as concentrations and total quantity of emission. The exhaust gas and/or sooty dust additionally contain various heavy metals such as cadmium, chromium and mercury, although they are present in extremely small quantities. Recently, a serious problem for the protection of environment has been posed by hydrogen fluoride (HF) and dioxins which are present in the exhaust gas although they are present also in extremely small quantities.

As for dioxins, the Japanese Ministry of Public Welfare laid down "Preventive guideline against generation of dioxins due to refuse disposal" from the viewpoint that it is desirable to minimize generation as well as emission of dioxins from these facilities into the environment. To prevent or at least minimize dioxins from being generated and emitted from garbage incinerating facilities in accordance with this guideline, addition of suitable neutralizer and/or adsorbent may be utilized or so-called dioxins decreasing condition including a combustion temperature (Temperature), a combustion time (Time) and a turbulence during combustion (Turbulence) in the incinerator may be adjusted depending on various factors such as a total quantity of generated dioxins.

To minimize generation of dioxins, the previously mentioned factors, particularly, the concentration and/or total quantity of dioxins which are being generated must be measured and thereby the current situation must be seized as accurately as possible. However, such measurement is difficult and requires a very expensive analyzer or the like, since the quantity of dioxins contained in the exhaust gas emitted into the atmosphere is extremely small. To solve this problem, it is well known, e.g., as described in Japanese Patent Application Disclosure Gazette No. 1992-161849, to utilize precursors of dioxins such as chlorobenzene and chlorophenol as substitute indices for the measurement.

According to this Patent Application Disclosure Gazette No. 1992-161849, after a quantity of the exhaust gas has been collected from the flue of garbage incinerating facilities, chlorobenzene sampling tube is taken out from the collector and the measurement is carried out using gas chromatography. Such a procedure of measurement necessarily takes a lot of time before the results of measurement can be reflected on the condition under which the operation of the incinerator should be operated.

In order to reflect the results of measurement on the operation of the incinerator, components contained in the exhaust gas must be continuously measured and, in view of this fact, Japanese Patent Application Disclosure Gazette No. 1993-312796 proposed a system for semi-continuous measurement/monitoring of chlorobenzene. However, this system is not adapted for direct measurement of dioxins but adapted for measurement of the substitute substances such as chlorobenzene on the basis of sample gas obtained by pretreating the exhaust gas so as to remove therefrom concomitant moisture and dust. Accordingly, there remains an apprehension that the results of measurement might be prevented from being rapidly and accurately reflected on the condition under which the incinerator should be operated.

On the other hand, the exhaust gas from the incinerator or the like has conventionally been guided to pass through various dust collectors before the exhaust gas is emitted into the atmosphere in order that the regulated substances and the other air polluting substances can be effectively collected from the exhaust gas before they are emitted into the atmosphere.

However, it becomes difficult to trap an adequate quantity of the air polluting substances as the dust collecting efficiency of the dust collector is deteriorated. To restore the desired dust collecting efficiency, cleaning and/or part-exchanging of the dust collector have usually been periodically carried out.

Conventionally, factors such as concentration of the regulated substances and the other air polluting substances contained in the exhaust gas have been detected and assessed according to the prescriptions by Japanese Industrial Standards to avoid the possibility that amounts of these undesirable substances higher than the critical values might be emitted. However, it is substantially impossible to perform detection and assessment in a continuous manner since detection and assessment also are performed on the basis of the sample gas having been subjected to the pretreatment suitable for every one of these substances as in the case of the previously mentioned measurement of chlorobenzene or the like. Consequently, the second best countermeasure has usually been adopted such that the sample gas is periodically collected from the flue and analyzed before the exhaust gas is emitted into the atmosphere.

If the result of measurement indicates that the air polluting substances contained in the sample gas exceed the respective standard values, such result may be sometimes due to an unexpected variation occurring in the condition under which the incinerator operates and/or the deteriorated efficiency of the dust collector. In this case, even if the dust collector is cleaned and/or the parts thereof are exchanged on the basis of measurement data, a certain quantity of the air polluting substances has already been emitted up to that time. In view of this fact, the cleaning of the dust collector and/or the exchange of parts thereof have usually been carried out independently of measurement of the sample gas and at the intervals of a sufficiently short period to minimize emission of the air polluting substances. As a consequence, the cleaning of the dust collector and/or the exchange of parts thereof must be frequently repeated. Frequent cleaning is time consuming and requires much labor, on one hand, and frequent exchange of parts correspondingly increases the maintenance cost.

SUMMARY OF THE INVENTION

In view of the problem as has been described above, it is a first object of the invention to provide a combustion system for sooty smoke generating facilities including an operating condition readjuster adapted to measure and monitor exhaust gas generated from a combustion furnace substantially in continuous mode and thereby to reflect a result of such measurement and monitoring on a condition under which the combustion furnace should be operated so that air polluting substances contained in the exhaust gas may be effectively collected.

The operation controller incorporated in this combustion system for the sooty smoke generating facilities should allow various components contained in the exhaust gas to be continuously monitored and thereby allow a variation occurring in these components to be continuously measured.

In view of such requirements and based on the findings that the concentrations of air polluting substances contained in the exhaust gas gradually increase even after having been treated by a dust collector as the dust collecting efficiency of the dust collector gradually deteriorates, on one hand, and the operation controller allows the exhaust gas to be continuously measured on the other hand, it is the second object of the invention to provide a combustion system for sooty smoke generating facilities including an instrument allowing the dust collecting efficiency of the dust collector to be continuously measured so as to minimize the frequency at which the dust collector should be cleaned and/or part-exchanged and thereby to alleviate the labor for cleaning as well as the cost for parts.

To achieve the objects set forth above, the invention provides a combustion system for sooty smoke generating facilities in which a post-treatment stage for combustion exhaust gas is provided closely adjacent an outlet of a combustion furnace and the combustion exhaust gas is emitted into the atmosphere after having passed through the post-treatment stage, the combustion system comprising an analyzer adapted to composition-analyze the combustion exhaust gas generated from the combustion furnace, a controller adapted to process an analytical signal provided from the analyzer and to output a control signal based on the analytical signal, a neutralizer supplier adapted to, upon receipt of the control signal from the controller, supply the combustion furnace with neutralizers of predetermined types, and an operating condition readjuster adapted to, upon receipt of the control signal from the controller, change at least one of the combustion temperature and the combustion time period of the combustion furnace and the turbulence condition during combustion so as to readjust the operating condition of the combustion furnace, wherein the combustion exhaust gas is introduced from a spot adjacent the outlet of the combustion furnace into the analyzer and wherein, based on the control signal, the neutralizer supplier supplies the combustion furnace with the neutralizers by quantities sufficient to neutralize quantities of respective components contained in the combustion exhaust gas and the operating condition readjuster controllably readjusts the operating condition of the combustion furnace.

Composition of the combustion exhaust gas being present on a spot adjacent the outlet of the combustion furnace is measured by the analyzer which applies, in turn, the controller with an analytical signal based on a result of the measurement. In response to this analytical signal, the controller selects particular types and quantities of neutralizers to be thrown into the combustion furnace in order to neutralize the components which have been determined to have concentrations higher than respectively predetermined values. Simultaneously, the controller applies the neutralizer supplier and the operating condition readjuster with control signals. The control signals associated with the operating condition readjuster instructs the readjuster to change the combustion temperature, the combustion time period and/or the turbulence condition and thereby to achieve controllable changing of the various factors such as the combustion temperature. The neutralizer supplier, upon receipt of the control signals associated with the controller, supplies the combustion furnace with particular types and quantities of neutralizers instructed by the associated control signals. In this way, the air polluting substances contained in the exhaust gas are neutralized and/or the operating condition of the combustion furnace is readjusted so as to suppress generation of the air polluting substances. As a result, emission of the air polluting substances is effectively suppressed.

Concentration of every component contained in the combustion exhaust gas determined at the spot closely adjacent the outlet of the combustion furnace is sufficiently high to facilitate composition-analysis of the exhaust gas. Among all, dioxins contained in the exhaust gas to be measured at the spot closely adjacent the outlet of the combustion furnace are at clearly detectable concentrations, since this analysis is carried out before the exhaust gas passes through the post-treatment stage.

The exhaust gas to be analyzed are of high component-concentrations, allowing the components of the exhaust gas to be continuously measured and monitored.

Measurement carried out at the spot closely adjacent the outlet of the combustion furnace is advantageous in that the demand for supplying the combustion furnace with neutralizers as well as the demand for readjusting the operating condition of the combustion furnace can be rapidly determined and the result of this measurement can be rapidly reflected upon the operating condition of the combustion furnace. Even when the substances to be incinerated are changed, emission of the air polluting substances can be rapidly suppressed.

It should be understood that suitable display and suitable printing such as a plotter may be connected to the controller to display and print the result of the measurement.

The invention provides also a combustion system for sooty smoke generating facilities in which a post-treatment stage for combustion exhaust gas is provided closely adjacent an outlet of the combustion furnace and the combustion exhaust gas is emitted into the atmosphere after having passed through the post-treatment stage, the combustion system comprising a first analyzer adapted to be supplied with the combustion exhaust gas directly from a spot closely adjacent the outlet of the combustion furnace and to composition-analyze the combustion exhaust gas, a second analyzer adapted to composition-analyze the combustion exhaust gas flowing from the post-treatment stage toward a chimney stack, a controller adapted to process an analytical signal provided from the first analyzer and to output a control signal based on the analytical signal, a neutralizer supplier adapted to, upon receipt of the controller signal provided from the controller, supply the combustion furnace with neutralizers of predetermined types, and an operating condition readjuster adapted to, upon receipt of the control signal provided from the controller, change at least one of a combustion temperature and a combustion time period of the combustion furnace and a turbulence condition during combustion so as to readjust the operating condition of the combustion furnace, wherein, based on the control signal, the neutralizer supplier supplies the combustion furnace with the neutralizers by quantities sufficient to neutralize the quantities of respective components contained in the combustion exhaust gas and an operating condition readjuster controllably readjusts the operating condition of the combustion furnace, and wherein the second analyzer monitors the composition of the combustion exhaust gas to be emitted into the atmosphere.

In response to the analytical signal provided from the first analyzer, neutralizers are supplied to the combustion furnace and/or the operating condition of the combustion furnace such as the combustion temperature is changed.

The air polluting substances contained in the combustion exhaust gas generated from the combustion furnace are collected as the combustion exhaust gas passes through the post-treatment stage and then emitted through the chimney stack into the atmosphere. The exhaust gas is introduced into the second analyzer from the flue extending between the post-treatment stage and the chimney stack and analyzed by the second analyzer. In this way, the exhaust gas before being emitted into the atmosphere is reliably monitored.

The analytical result obtained by the second analyzer may be transmitted to a display and/or a printer so as to be displayed and/or printed. It is also possible to transmit the analytical signal to the controller so that, in response to this analytical signal just as in response to the analytical signal provided from the first analyzer, the controller provides control signals to the neutralizer supplier and the operating condition readjuster so that the neutralizer may be supplied to the combustion furnace and the operating condition of the combustion furnace may be controllably readjusted.

It is desirable that the exhaust gas can be measured by the first analyzer also before the exhaust gas reaches the chimney stack and at the same time the facilities can be constructed in a scale as small as possible. To achieve this, the invention provides a combustion system for sooty smoke generating facilities in which a post-treatment stage for combustion exhaust gas is provided closely adjacent an outlet of a combustion furnace and the combustion exhaust gas is emitted into the atmosphere after having passed through the post-treatment stage, the combustion system comprising an analyzer adapted to composition-analyze the combustion exhaust gas, a controller adapted to process an analytical signal provided from the analyzer and to output a control signal based on the analytical signal, a neutralizer supplier adapted to, upon receipt of the control signal provided from the controller, supply the combustion furnace with neutralizers of predetermined types, an operating condition readjuster adapted to, upon receipt of the control signal provided from the controller, change at least one of a combustion temperature and a combustion time period of the combustion furnace and a turbulence condition during combustion so as to controllably readjust the operating condition of the combustion furnace, a first duct through which the combustion exhaust gas is introduced from a spot adjacent the output of the combustion furnace into the analyzer, a second duct through which the combustion exhaust gas flowing from the post-treatment stage toward a chimney stack is introduced into the analyzer, and duct switcher serving to switch the first and second ducts from one to another at predetermined time intervals, wherein, based on the control signal depending on an analytical result of the combustion exhaust gas introduced through the first duct, the neutralizer supplier supplies the combustion furnace with the neutralizers by quantities sufficient to neutralize the quantities of components contained in the combustion exhaust gas, on one hand, and the operating condition readjuster controllably readjusts the operating condition of the combustion furnace, on the other hand, and wherein the composition of the combustion exhaust gas to be emitted into the atmosphere is monitored on the basis of the analytical result of the combustion exhaust gas introduced through the second duct.

The controller may be connected to a suitable display and/or a printer such as a plotter to display and/or print an analytical result obtained from the exhaust gas sampled before it reaches the chimney stack. It is also possible to display and/or print an analytical result obtained from the exhaust gas sampled at the spot closely adjacent the outlet of the combustion furnace.

The time intervals at which the measuring spots are switched may be adjusted in consideration of a time period taken before the combustion exhaust gas generated from the combustion furnace reaches the chimney stack to measure the exhaust gas improved by addition of the neutralizers and/or change of the operating condition. In this manner, the exhaust gas can be continuously monitored.

It is also desirable that a dust collecting efficiency of the dust collector can be continuously monitored. To achieve this, the invention provides a combustion system for sooty smoke generating facilities in which a post-treatment stage for combustion exhaust gas is provided closely adjacent an outlet of a combustion furnace and the combustion exhaust gas is emitted into the atmosphere after having passed through the post-treatment stage, the combustion system comprising a dust collector provided in the post-treatment stage for combustion exhaust gas to collect predetermined substances contained in the exhaust gas generated from the combustion furnace, a first analyzer adapted to be supplied with the exhaust gas from a flue extending between the combustion furnace and the dust collector and to composition-analyze the exhaust gas, a second analyzer adapted to be supplied with the exhaust gas from a flue extending between the dust collector and an outlet immediately into the atmosphere and to composition-analyze the exhaust gas, and a controller adapted to be applied with analytical signals from the first analyzer and second analyzer, respectively, wherein the controller calculates a ratio between a concentration of a given substance determined by the first analyzer and a concentration of this substance determined by the second analyzer and measures a dust collecting efficiency of the dust collector on the basis of this concentration ratio.

Every component of the exhaust gas presents a relatively high concentration immediately after being generated from the combustion furnace. Accordingly, the first analyzer functions to analyze the components of relatively high concentrations. On the other hand, every component of the exhaust gas having passed through the dust collector presents a relatively low concentration because the majority of these components have already been collected. Accordingly, the second analyzer functions to analyze the components of relatively low concentrations. So far as the dust collector maintains a predetermined dust collecting efficiency, initial high concentrations of the components can be lowered to predetermined levels. Deterioration of the dust collecting efficiency makes it impossible. Specifically, a variation in the concentration ratio before and after the dust collector corresponds to a variation in the dust collecting efficiency and it is possible to determine the dust collecting efficiency based on this variation in the concentration ratio. The first and second analyzers composition-analyze the exhaust gas generated substantially at the same time to calculate the concentration ratio, i.e., the exhaust gas partially sampled for the first analyzer is introduced into the second analyzer. Accordingly, composition-analysis by the second analyzer is delayed until the exhaust gas having been introduced into the first analyzer reaches the sampling spot for the second analyzer.

If it is determined on the basis of a measured dust collecting efficiency that the dust collector is not operating with a desired dust collecting efficiency, the dust collector is cleaned or parts thereof are exchanged to restore the desired dust collecting efficiency. It is important for the operator to leave a margin when the dust collecting efficiency is determined to have deteriorated so that the air polluting substances can be reliably prevented from being emitted together with the exhaust gas before determination of such deterioration.

Cleaning and/or part-exchange is carried out only when the dust collecting efficiency is determined to fall below the predetermined level instead of such cleaning and/or part-exchange being carried out periodically regardless of the dust collecting efficiency. In this manner, the frequencies and labors required for the cleaning and/or part-exchange are alleviated and the cost for parts is also reduced.

It is desirable to measure a variation of the dust collecting efficiency while the operating condition of the combustion furnace is controlled and thereby to minimize the frequencies at which the dust collector should be cleaned and/or parts thereof should be exchanged. To achieve this, the invention provides a combustion system for sooty smoke generating facilities in which a post-treatment stage for combustion exhaust gas is provided closely adjacent an outlet of a combustion furnace and the combustion exhaust gas is emitted into the atmosphere after having passed through the post-treatment stage, the combustion system comprising a dust collector provided in the post-treatment stage for the combustion exhaust gas to collect predetermined substances contained in the exhaust gas generated from the combustion furnace, a first analyzer adapted to be supplied with the exhaust gas from a flue extending between the combustion furnace and the dust collector and to composition-analyze the exhaust gas, a second analyzer adapted to be supplied with the exhaust gas from a flue extending between the dust collector and an outlet immediately into the atmosphere, a controller adapted to be applied with analytical signals from the first analyzer and second analyzer, respectively, a neutralizer supplier adapted to, upon receipt of an operation control signal provided by the controller as a result of processing the analytical signal from the first analyzer, supply the combustion furnace with neutralizers of predetermined types, and an operating condition readjuster adapted to, upon receipt of the operation control signal, change at least one of a combustion temperature and a combustion time period of the combustion furnace and a turbulence condition during combustion so as to controllably readjust the operating condition of the combustion furnace, wherein the controller calculates a ratio between a concentration of a given substance determined by the first analyzer and a concentration of this substance determined by the second analyzer and measures a dust collecting efficiency of the dust collector on the basis of the concentration ratio, and wherein, based on the operation signal, the neutralizer supplier supplies the combustion furnace with the neutralizers by quantities sufficient to neutralize respective components contained in the exhaust gas and the operating condition readjuster controllably readjusts the operating condition of the combustion furnace.

It is desirable to employ a single analyzer and thereby not only to reduce a cost of the entire facilities but also to miniaturize the analyzer. To achieve this, the invention provides a combustion system for sooty smoke generating facilities in which a post-treatment stage for combustion exhaust gas is provided closely adjacent an outlet of a combustion furnace and the combustion exhaust gas is emitted into the atmosphere after having passed through the post-treatment stage, the combustion system comprising a dust collector provided in the post-treatment stage for the combustion exhaust gas to collect predetermined substances contained in the exhaust gas generated from the combustion furnace, an analyzer adapted to composition-analyze the exhaust gas, a controller adapted to process an analytical signal provided from the analyzer, a first duct through which the exhaust gas is introduced into the analyzer from a flue extending between the combustion furnace and the dust collector, a second duct through which the exhaust gas is introduced into the analyzer from a flue extending between the dust collector and an outlet immediately into the atmosphere, and a duct switcher adapted to switch the first and second ducts from one to another at predetermined time intervals, wherein the controller calculates a ratio between a concentration of a given substance contained in the exhaust gas introduced through the first duct and a concentration of this substance contained in the exhaust gas introduced through the second duct and measures a dust collecting efficiency of the dust collector on the basis of the concentration ratio.

It is desirable to employ the single analyzer and to measure a variation in the dust collecting efficiency simultaneously with control of the operating condition under which the combustion furnace should operate. To achieve this, the invention provides a combustion system for sooty smoke generating facilities in which a post-treatment stage for the combustion exhaust gas is provided closely adjacent an outlet of a combustion furnace and the combustion exhaust gas is emitted into the atmosphere after having passed through the post-treatment stage, the combustion system comprising a dust collector provided in the post-treatment stage of the combustion furnace to collect predetermined substances contained in the exhaust gas generated from the combustion furnace, an analyzer adapted to composition-analyze the exhaust gas, a controller adapted to process an analytical signal provided from the analyzer, a first duct through which the exhaust gas is introduced into the analyzer from a flue extending between the combustion furnace and the dust collector, a second duct through which the exhaust gas is introduced into the analyzer from a flue extending between the dust collector and an outlet immediately into the atmosphere, a duct switcher adapted to switch the first and second ducts from one to another at predetermined time intervals, a neutralizer supplier adapted to, upon receipt of an operating control signal provided by the controller as a result of processing the analytical signal from the analyzer depending on the combustion exhaust gas introduced through the first duct, supply the combustion furnace with neutralizers of predetermined types, and an operating condition readjuster adapted to, upon receipt of the operation control signal, change at least one of a combustion temperature and a combustion time period of the combustion furnace and a turbulence condition during combustion so as to readjust the operating condition of the combustion furnace, wherein the controller calculates a ratio between a concentration of a given substance contained in the exhaust gas introduced through the first duct and a concentration of this substance contained in the exhaust gas introduced through the second duct and measures a dust collecting efficiency of the dust collector on the basis of this concentration ratio and wherein, based on the operation control signal, the neutralizer supplier supplies the combustion furnace with the neutralizers by quantities sufficient to neutralize respective components contained in the exhaust gas and the operating condition readjuster controllably readjusts the operating condition of the combustion furnace.

The dust collector is preferably provided in the form of a bag filter. In view of the fact that the combustion exhaust gas is emitted into the atmosphere after having passed through the dust collector, it is desirable to monitor a composition of the combustion exhaust gas being emitted into the atmosphere on the basis of concentrations of the predetermined substances determined by the second analyzer or by the single analyzer after having been introduced through the second duct into this single analyzer.

When the concentration ratios fall below the predetermined values, a deterioration of the dust collecting efficiency is suggested and cleaning and/or part-exchange is instructed. In view of this fact, the combustion system preferably further comprises an alarm adapted to be actuated upon receipt of an alarm signal provided from the controller wherein the controller provides the alarm signal when the concentration ratios calculated by the controller fall below the respective predetermined values.

The analyzer should accurately and reliably analyze a composition of the combustion exhaust gas particularly when the component concentrations are relatively high. To achieve this, the analyzer is provided preferably in the form of an infrared spectroscopic analyzer. To measure precursors of the air polluting substances as the corresponding substitute indices, the analyzer is provided preferably in the form of a measuring instrument for CO or $O_2$. Particularly for dioxins, from the viewpoint that the measuring precursors of dioxins, the analyzer is provided preferably in the form of a measuring instrument for precursors of dioxins such as chlorophenol, chlorobenzene or PCB (polychlorinated biphenyl).

DETAILED DESCRIPTION OF THE EMBODIMENTS

Details of the inventive combustion system for sooty smoke generating facilities will be more fully understood from the description of specific embodiments given hereunder in reference with the accompanying drawings. It should be understood here that, in the following description, garbage incinerating facilities will be discussed as a specific example of the sooty smoke generating facilities and the garbage incinerating system in such facilities will be described as a specific example of the inventive combustion system.

Figure 1:
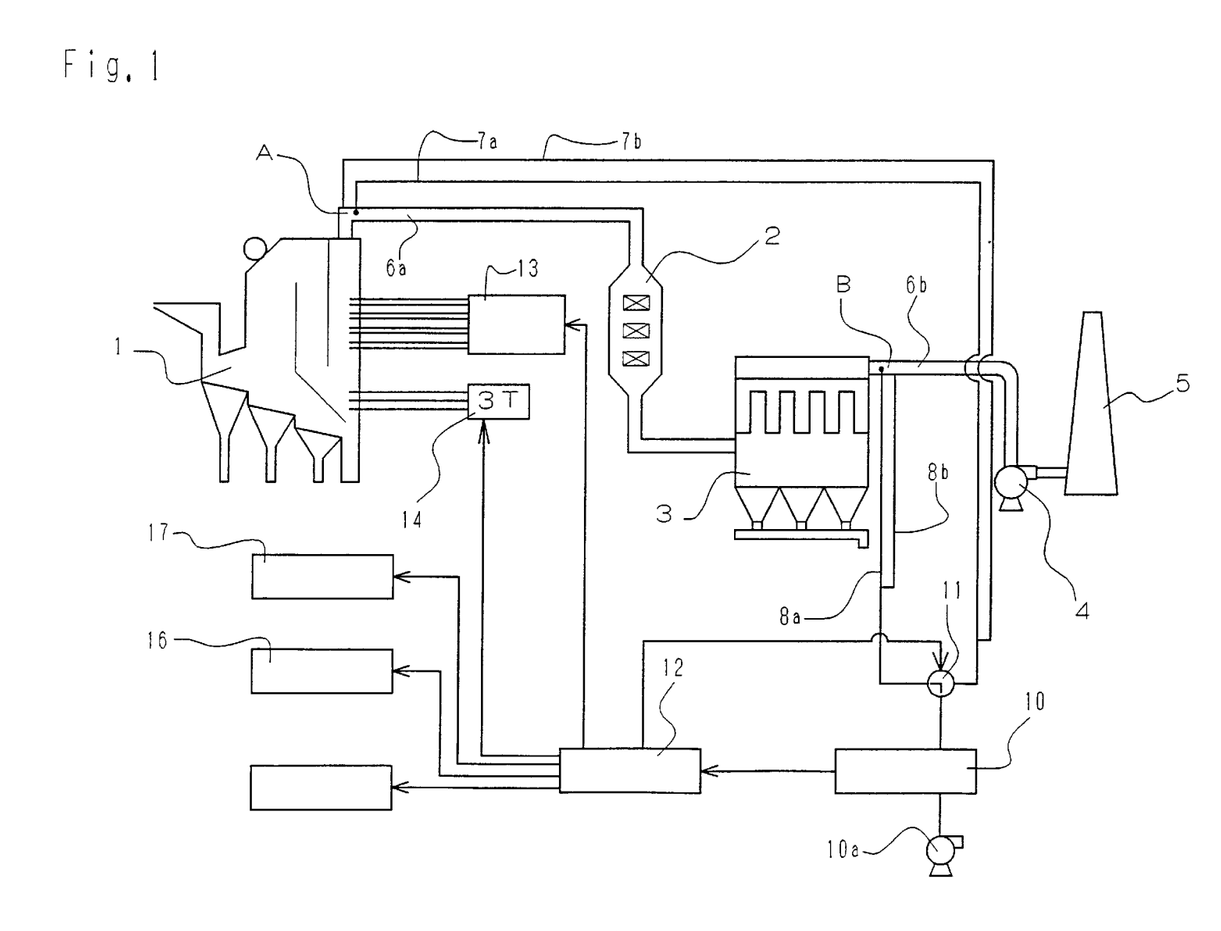
FIG. 1 is a structural diagram schematically illustrating the inventive combustion system for sooty smoke generating facilities.

FIG. 1 is a structural diagram schematically illustrating such garbage incinerating system. Combustible garbage to be incinerated is thrown into a combustion furnace in the form of a garbage incinerator 1 and combusted therein. Combustion exhaust gas generated during combustion in the garbage incinerator 1 is appropriately cooled as it passes through a heat exchanger 2 forming a post-treatment stage, then fed to a dust collector 3 in which various predetermined substances are collected from the exhaust gas, thereafter fed by an induced draft fan 4 to a chimney stack 5 and finally emitted into the atmosphere. The dust collector 3 may be selected from a group consisting of a cyclone dust collector, an electric precipitator, a bag filter or the like and a combination thereof depending on the particular substances to be collected. The present embodiment employs the bag filter in view of the fact that a mass of dust appropriately accumulating on filter cloth at a high dust collecting efficiency advantageously improve a filtration effect so that even extremely fine particles can be collected. If desired, slaked lime in powdery form may be blown into a zone defined in front of the dust collector or a smoke washing device may be provided in this zone for more effective collection of the air polluting substances such as hydrogen chloride and sulfur oxides.

Figure 2:
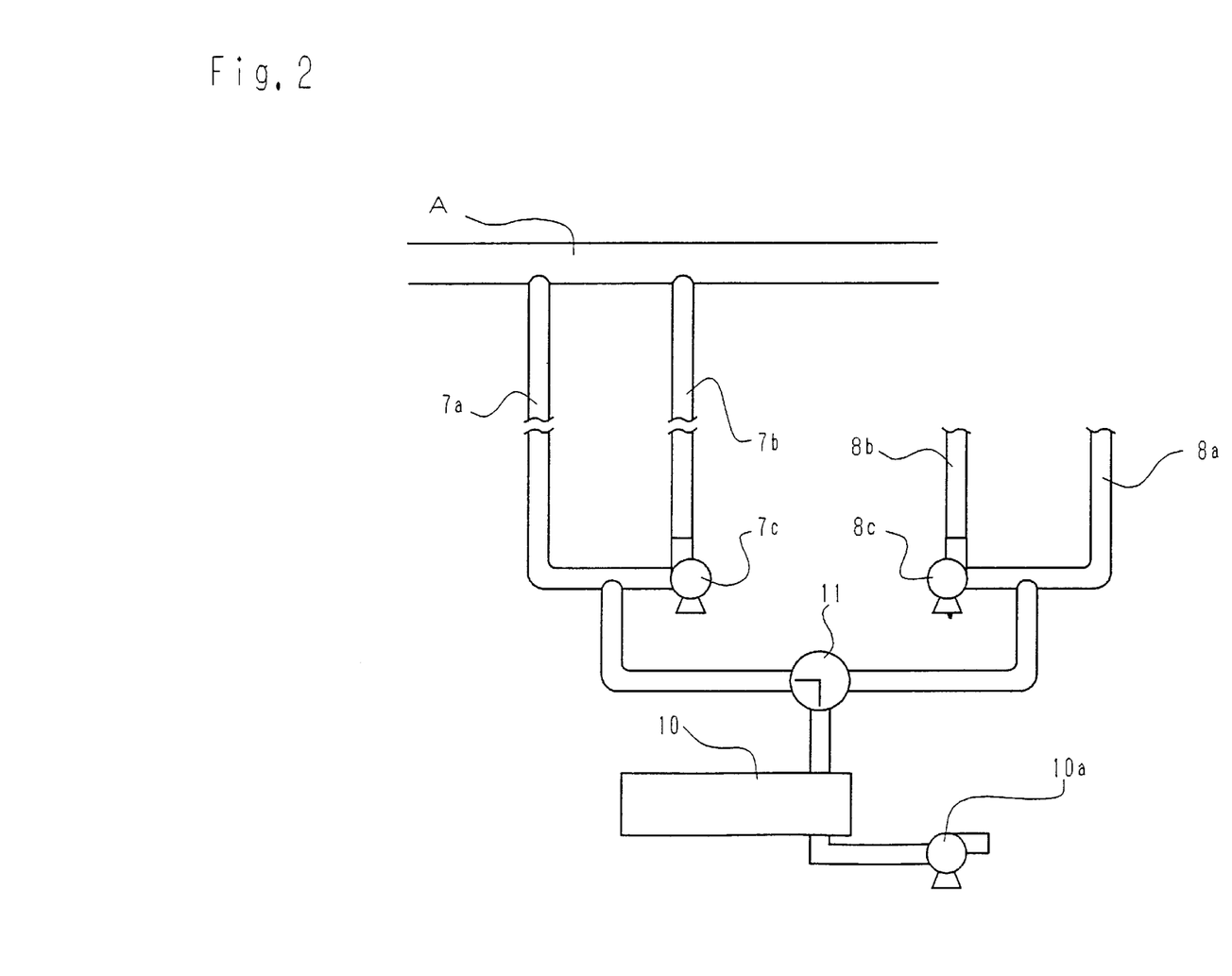
FIG. 2 is a structural diagram schematically illustrating a collector section functioning to collect sample gas and to supply this to the analyzer.

At a measuring spot A corresponding to the inlet of a flue 6a through which the combustion exhaust gas is guided from the garbage incinerating furnace 1 to the heat exchanger 2, i.e., lying adjacent the outlet of the garbage incinerating furnace 1, a quantity of combustion exhaust gas is collected by a collecting duct 7a. This collecting duct 7a communicates via a switching valve 11 serving as a duct switcher with an infrared spectroscopic gas analyzer 10. A return duct 7b is connected to the inlet of the flue 6a at the measuring spot A and, as seen in FIG. 2, communicates with the outlet of an induced draft fan 7c. The inlet of this induced draft fan 7c communicates with the collecting duct 7a at an intermediate point along the collecting duct 7a. The infrared spectroscopic gas analyzer 10 is adapted to be supplied with sample gas under the action of an induced draft fan 10a.

At a measuring spot B provided along a flue 6b extending from the dust collector 3 to the chimney stack 5, the exhaust gas is collected by a collecting duct 8a. This collecting duct 8a communicates via the switching valve 11 with the infrared spectroscopic gas analyzer 10. A return duct 8b is connected to the flue 6b at the measuring spot B and communicates, like the return duct 7b, with the outlet of the inducted draft fan 8c. The inlet of this induced draft fan 8c communicates with the collecting duct 8a at an intermediate point therealong.

Figure 3:
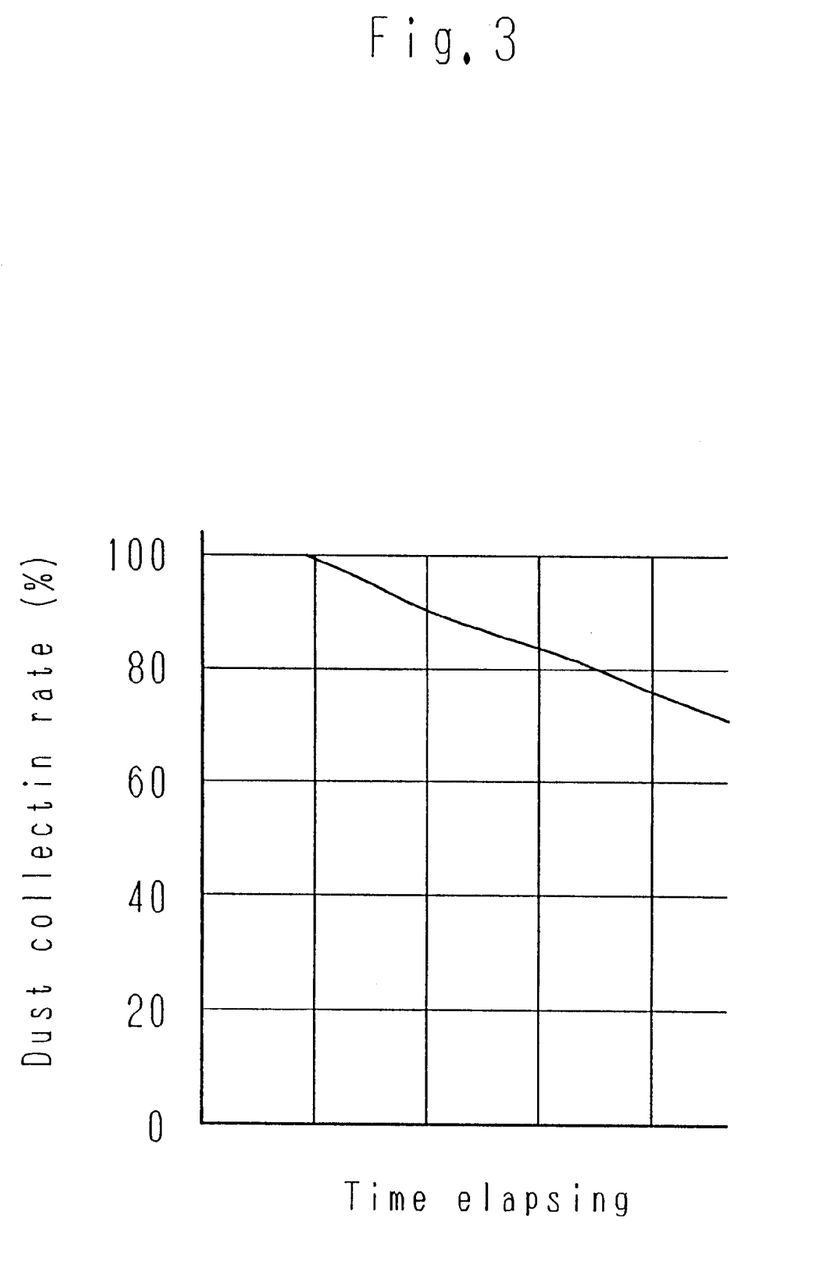
FIG. 3 is a graphic diagram plotting the dust collecting efficiency varying as the time elapses.

An output signal provided from the infrared spectroscopic gas analyzer 10 is applied as an analytical signal to controller 12. Based on the analytical signal, the controller 12 calculates a ratio between the concentrations determined on the component substance of the exhaust gas at the measuring spot A and at the measuring spot B and compares the concentration ratio thus calculated with a predetermined reference value of concentration ratio. Obviously, the concentration determined at the measuring spot A is relatively high and the concentration determined at the measuring spot B is relatively low. Accordingly, the concentration ratio calculated when the dust collector 3 is properly operating is higher than the concentration ratio calculated when the dust collector 3 has its collecting function deteriorated. In other words, the reference value of concentration ratio is a threshold on the basis of which it is determined whether the dust collector 3 is fulfilling its expected function or not. The concentration ratio less than this reference value of concentration ratio suggests that the dust collector 3 has its dust collecting efficiency correspondingly deteriorated. FIG. 3 is a graphic diagram plotting the dust collecting efficiency varying as the time elapses. As will be apparent from this graphic diagram, the dust collecting efficiency is deteriorated as the time elapses. The reference value of concentration ratio may be set up to a value leaving a sufficient margin before the critical value for collection of the air polluting substances is reached, for example, to a value corresponding to 85% of the nominal collecting efficiency which should be achieved by the dust collector installed in the combustion system. When the concentration ratio falls below the reference value of concentration ratio, an alarm signal is output from the controller 12. In addition to the alarm signal, the controller 12 outputs a concentration ratio signal which represents information on the current concentration ratio.

The alarm signal provided from the controller 12 is applied to the alarm 17 which, upon receipt of the alarm signal, activates an alarm buzzer or an alarm siren, or lights or turns on and off an alarm lamp.

The controller 12 determines also, on the basis of the analytical signal, whether the concentration or the other values of the air polluting substances contained in the combustion exhaust gas are less than the predetermined values or not. If the values are determined to be higher than the predetermined values, the controller 12 applies a control signal inclusive of instruction necessary to collect the air polluting substances to the neutralizer supplier 13 and the operating condition readjuster 14, respectively.

Figure 4:
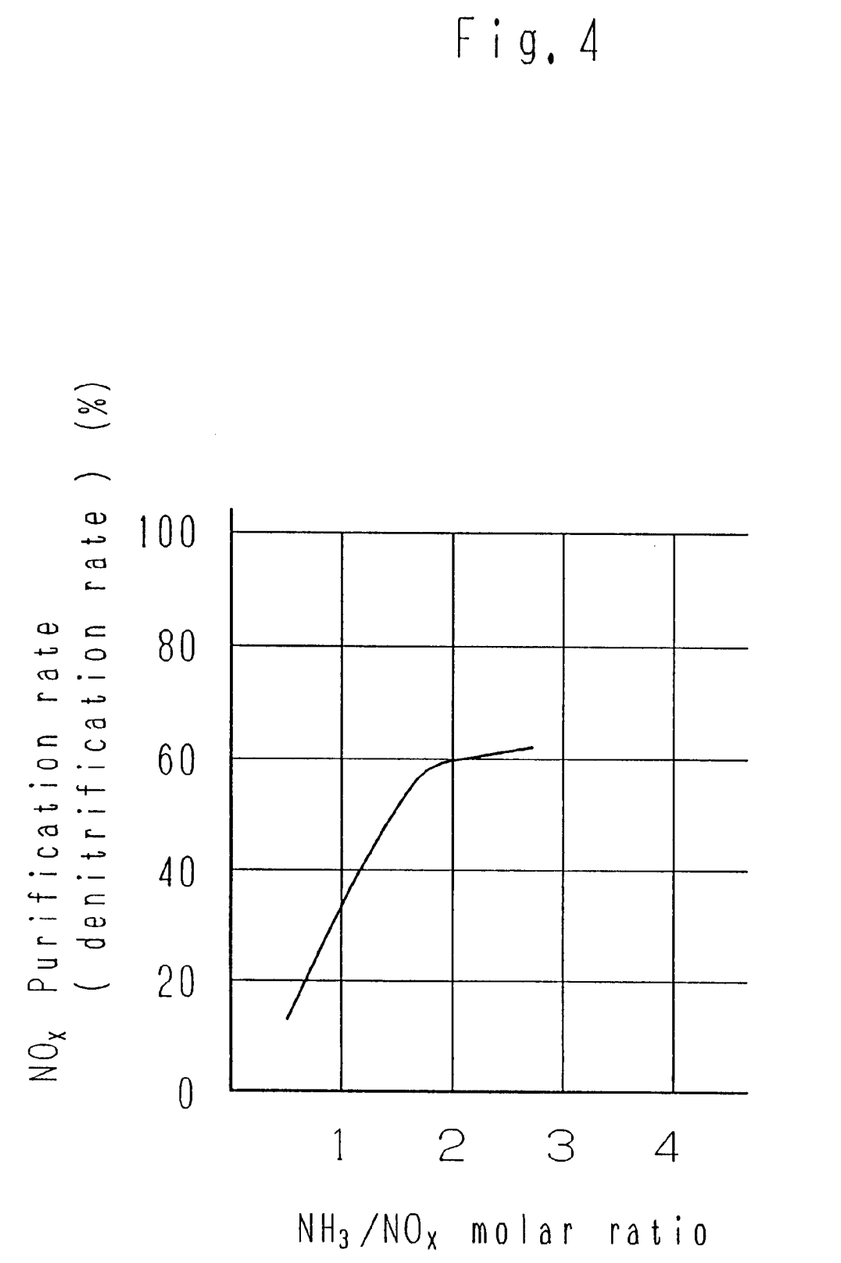
FIG. 4 is a graphic diagram plotting the dust purification efficiency depending on the quantity of ammonia used as the neutralizer for nitrogen oxides.
Figure 6:
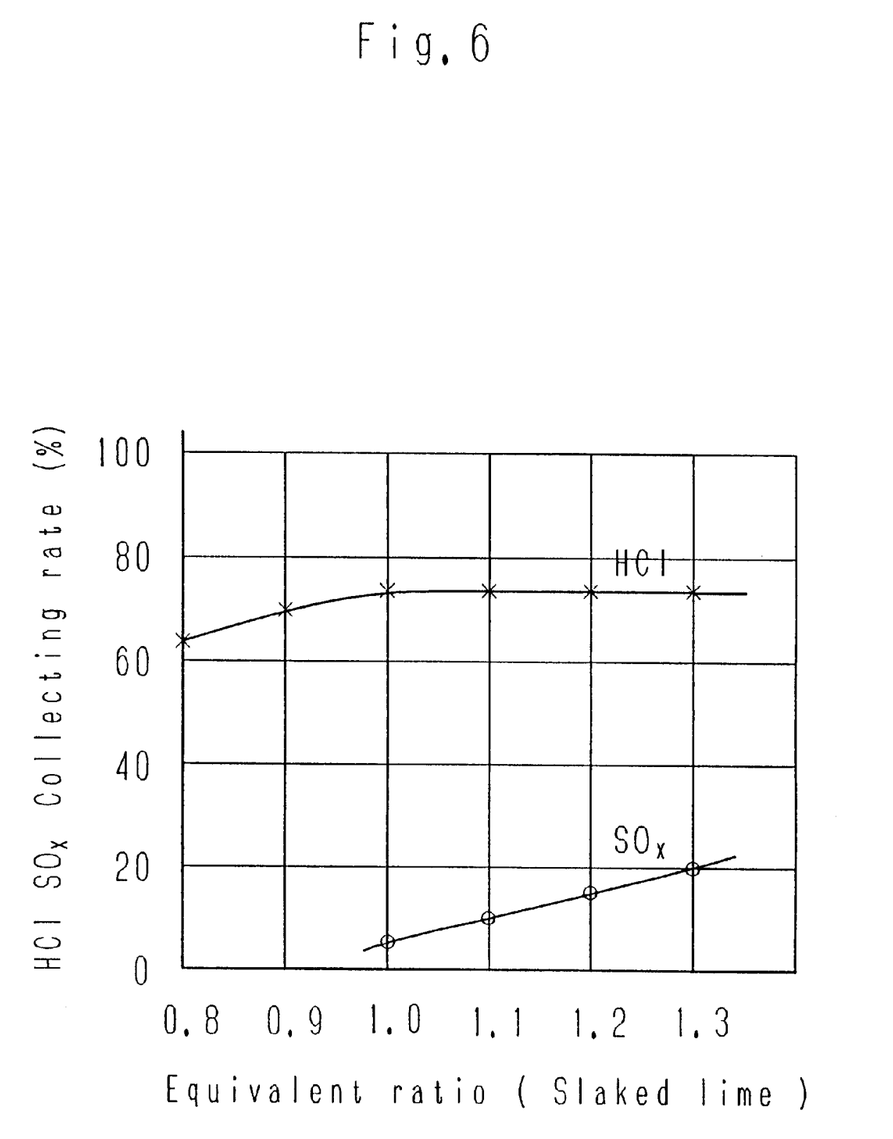
FIG. 6 is a graphic diagram plotting the collecting rate achieved by the slaked lime for hydrogen chloride and sulfur oxides, depending on the used quantity of the slaked lime.

Based on the control signal, the neutralizer supplier 13 supplies the garbage incinerating furnace 1 with the neutralizer. The neutralizer may be selected from those which are well known to be effective for this purpose. FIG. 4 is a graphic diagram plotting the purification rate versus ammonia ($NH_3$) used as the neutralizer, wherein the abscissa indicates $NH_3/No_x$ molar ratio. As will be apparent from FIG. 4, the purification rate is improved as the quantity of neutralizer increases. FIG. 6 is a graphic diagram plotting the collecting rate achieved by slaked lime for hydrogen chloride and sulfur oxides, wherein the abscissa indicates the equivalent ratio of slaked lime. As will be apparent from this graphic diagram, the collecting rate both for hydrogen chloride and sulfur oxides are improved as the quantity of slaked lime used as the neutralizer increases. It should be understood that the collecting rate for hydrogen chloride reaches its saturated state once the equivalent ratio of slaked lime has increased up to 1.0 and the collecting rate remains on the same level even if the equivalent ratio further increases.

Figure 5:
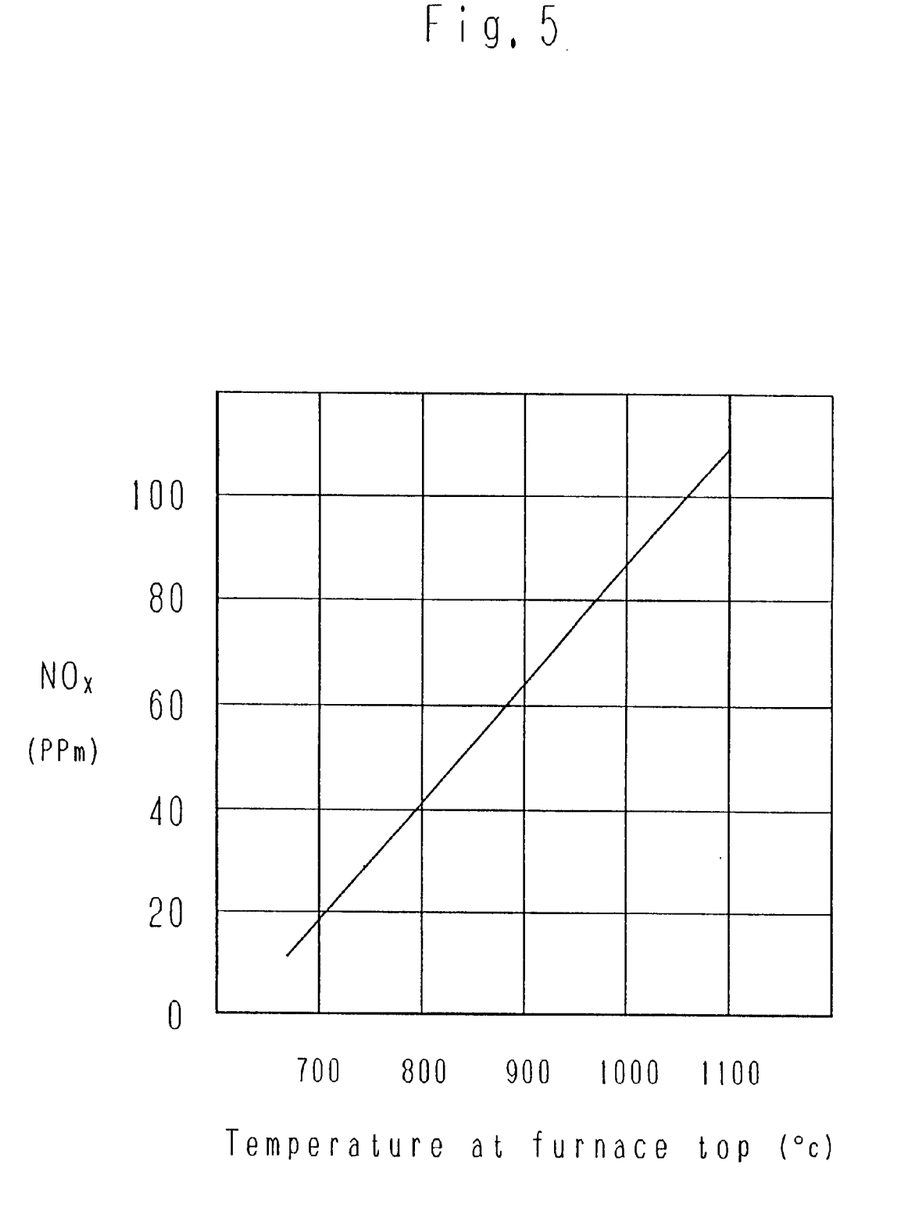
FIG. 5 is a graphic diagram plotting the relationship observed between nitrogen oxides and the temperature at upper part of the furnace.
Figure 7:
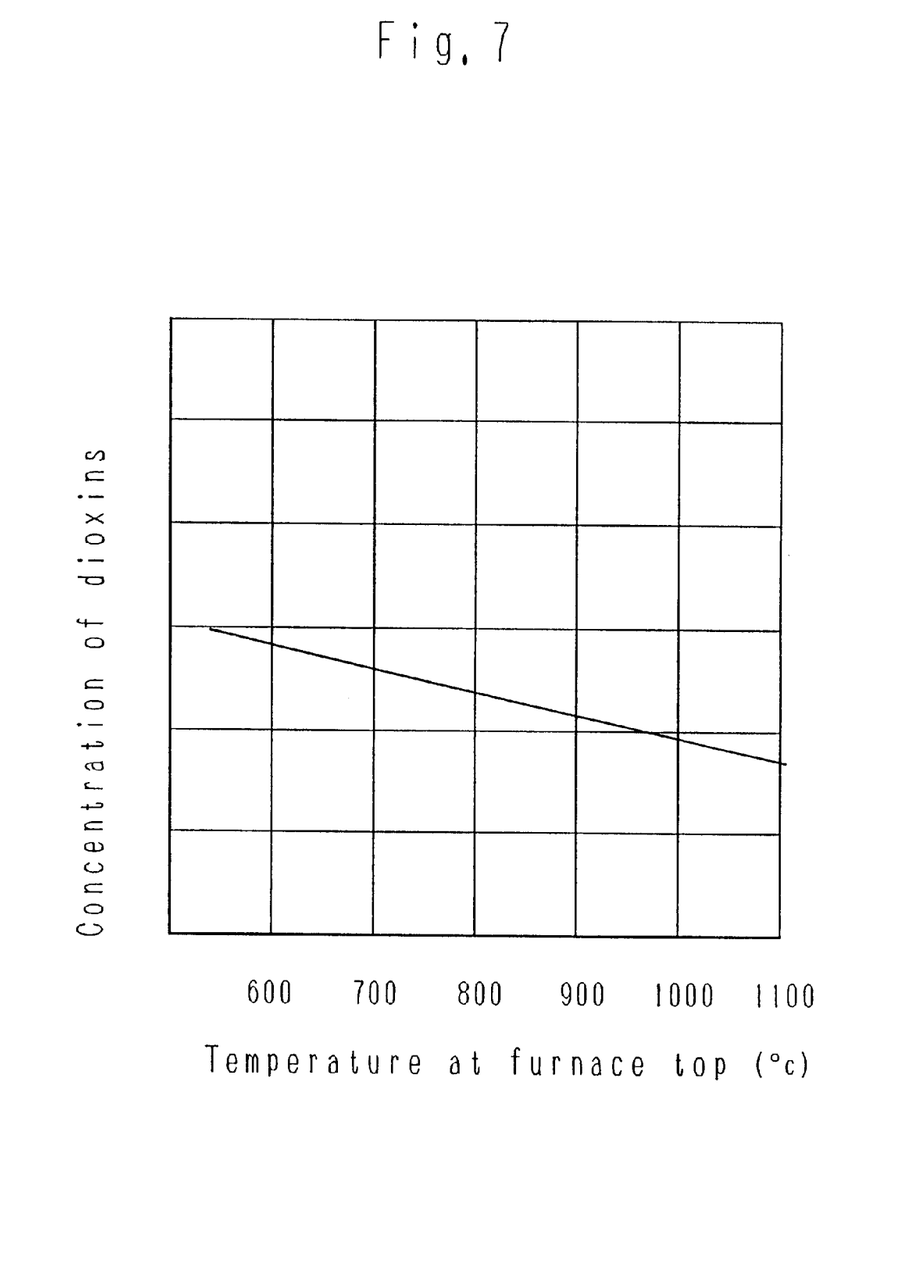
FIG. 7 is a graphic diagram plotting the relationship observed between dioxins and the temperature at upper part of the furnace.

The operating condition readjuster 14 controls the condition under which the garbage incinerating furnace 1 operates by adjusting all or any one of the factors such as combustion temperature as well as combustion time in the garbage incinerating furnace 1 and turbulence during combustion or a combination of these factors. It is well known to readjust the operating condition of the garbage incinerating furnace 1 during collection of the air polluting substances. FIG. 5 is a graphic diagram plotting a relationship observed between nitrogen oxides and the temperature at upper part of the furnace. This graphic diagram indicates that the generation of nitrogen oxides is promoted as the temperature rises. FIG. 7 is a graphic diagram plotting a relationship observed between dioxins and the temperature at the upper part of the furnace. As will be understood from this graphic diagram, the generation of dioxins decreases as the temperature rises. Based on such observation, it is the practice to incinerate the garbage in the furnace at a temperature of approximately 900–1200° C. and the combustion exhaust gas is rapidly cooled by the heat exchanger 2 to approximately 200° C. or lower. The incinerating furnace 1 is provided with various measuring instruments associated with the combustion temperature, the combustion time and the turbulence condition, respectively, so that respective measuring signals output from these measuring instruments are applied to the controller 12.

Additionally, the controller 12 supplies a display control signal to the co display 15, a print control signal to the printer 16 such as a plotter and a switching instruction signal to the switching valve 11. The display 15 is adapted to display an analytical result obtained by the infrared spectroscopic gas analyzer 10 and this analytical result is printed by the printer 16. The display 15 and printer 16 are adapted to display and print a variation in the concentration ratio upon receipt of the concentration ratio information signal from the controller 12.

The inventive combustion system for sooty smoke generating facilities constructed particularly in the form of the garbage incinerator as has been described hereinabove as well as the operation controller and the dust collecting efficiency measurer both incorporated in the inventive combustion system operate in manners as will be described.

Combustible garbage is transported to the garbage incinerating facilities and thrown into the garbage incinerating furnace 1. The combustion exhaust gas generated from the furnace 1 is guided from the furnace 1 through the flue 6a to the heat exchanger 2 in which the combustion exhaust gas is cooled to an appropriate temperature while the initial heat is used to preheat the air for combustion. Then the combustion exhaust gas is guided to the dust collector 3 which collects the polluting substances contained in the exhaust gas.

The exhaust gas having passed through the dust collector 3 is then guided to the chimney stack 5 under the suction by the induced draft fan 4 so as to ascend through the chimney stack 5 and to be emitted at a sufficiently high spot into the atmosphere. While the induced draft fan 4 provides a suction enough to guide the combustion exhaust gas so as to pass through the heat exchanger 2 and the dust collector 3, there may be provided an additional induced draft fan or forced draft fan at an appropriate location of the flue to guide the combustion exhaust gas more reliably.

The collecting duct 7a is connected to the flue 6a at the measuring spot A and the combustion exhaust gas is collected at the measuring point A through the collecting duct 7a under the suction of the induced draft fan 7c. The return duct 7b is connected to the outlet of the induced draft fan 7c and the outlet end of this return duct 7b communicates with the collecting duct 7a at the measuring spot A so that the induced draft fan 7c may cause the combustion exhaust gas to circulate through the collecting duct 7a and return duct 7b communicating with each other at the measuring spot A. At the measuring spot B also, the collecting duct 8a and return duct 8b communicate with each other so that the combustion exhaust gas may circulate through the collecting duct 8a and return duct 8b.

When the switching valve 11 is operated to bring the collecting duct 7a in communication with the infrared spectroscopic gas analyzer 10, on one hand, and the induced draft fan 7c is deenergized and the induced draft fan 10a is energized, on the other hand, the quantity of combustion exhaust gas stagnating in the collecting duct 7a and the return duct 7b is expelled to the infrared spectroscopic gas analyzer 10 by which the quantity of combustion exhaust gas is composition-analyzed at the measuring spot A. Similarly, when the switching valve 11 is operated so as to bring the collecting duct 8a in communication with the infrared spectroscopic gas analyzer 10, the quantity of combustion exhaust gas present at the measuring spot B is composition-analyzed.

The analytical result obtained by the infrared spectroscopic gas analyzer 10 is transmitted to the controller 12 which determines, based on the analytical result, whether the values characterizing the air polluting substances contained in the combustion exhaust gas, inclusive of the concentration values, are less than the predetermined values or not. If the characterizing values are determined to be higher than the predetermined values, the controller 12 supplies both the neutralizer supplier 13 and the operating condition readjuster 14 with the instruction necessary to collect the excessive quantity of the air polluting substances.

If nitrogen oxides are detected to be present in excess of the corresponding predetermined values, the neutralizer supplier 13 is instructed by the controller 12 to supply the garbage incinerating furnace 1 with the neutralizer such as bromine or ammonia. Upon receipt of this instruction, the neutralizer supplier 13 is actuated to throw the neutralizer into the garbage incinerating furnace 1. If dioxins are detected to be present in excess of the corresponding predetermined values, the operating condition readjuster 14 is instructed by the controller 12 to raise the furnace temperature. This instruction actuates the operating condition readjuster 14 to raise the combustion temperature.

Suitable types of neutralizer may be selectively used depending on the respective air polluting substances, e.g., bromine or ammonia for nitrogen oxides, sodium hydroxide (NaOH) or the like for sulfur oxides, compound of calcium such as calcium hydroxide [$Ca(OH)_2$], calcium oxide (CaO) or calcium carbonate ($CaCO_3$) for dioxins, and slaked lime or hydrated calcium silicate for hydrogen chloride. As for dioxins, there are available various types of adsorbent such as coke and activated carbon. Emission of dioxins can be suppressed, in addition to use of such adsorbent, by readjusting the operating factors of the garbage incinerator furnace 1 such as temperature, stagnating time and intermixing condition of gas components, more specifically, combustion temperature as well as combustion time and turbulence condition during combustion in the incinerating furnace. So-called low-oxygen operation is one of measures which has often been employed to suppress generation of nitrogen oxides. In this manner, the controller 12 instructs the neutralizer supplier 13 and the operation condition readjuster 14 to combine addition of the neutralizer with readjustment of the operating condition so that the air polluting substances may be collected under the optimal condition for the particular garbage incinerator.

The neutralizer thrown into the garbage incinerating furnace 1 reacts with the air polluting substances contained in the combustion exhaust gas to neutralize the air polluting substances. Simultaneously, the operating condition of the garbage incinerating furnace 1 is readjusted by the operating condition readjuster 14. These countermeasures alleviate or completely eliminate emission of the air polluting substances contained in the combustion exhaust gas into the atmosphere.

When the switching valve 11 is operated so as to bring the collecting duct 8a in communication with the infrared spectroscopic gas analyzer 10, the quantity of exhaust gas present at the measuring spot B is composition-analyzed. At the measuring spot B, the exhaust gas may still contain the air polluting substances but in most of cases the majority thereof has already been collected and there is no possibility that the quantities of air polluting substances might exceed the respective standard values. Accordingly, the analytical result obtained as at the measuring spot B is merely transmitted from the controller 12 to the display 15 and the printer so that the analytical result may be displayed and printed and it is not essential to reflect the analytical result upon collection of the air polluting substances.

However, should the exhaust gas still contain detectable quantities of air polluting substances at the measuring spot B, it may lead to pollution of the environment, since the exhaust gas having passed the measuring spot B is subjected to no more filtration and directly emitted into the atmosphere. To minimize such pollution, it is also possible to construct the combustion system so that the controller 12 applies the neutralizer supplier 13 and/or the operating condition readjuster 14 with a control signal which instructs these devices 13 and/or 14 to throw the neutralizer into the furnace and/or to readjust the operating condition of the furnace, respectively.

The measurement is alternately carried out at the measuring spots A and B at predetermined intervals by operating the switching valve 11. After the composition of the combustion exhaust gas has been improved by the neutralizer supplier 13 as well as the operating condition readjuster 14, a considerable time is taken before this improved exhaust gas reaches the measuring spot B. The measurement is carried out during a predetermined time period □T sufficient to assure that the improved exhaust gas can reach the measuring spot B and the measurement is switched to that at the measuring spot B after the time period $\Delta T$ has elapsed. After a predetermined time period has elapsed, the measurement is switched again to that at the measuring spot A. It is also possible to set the predetermined time period elapsing before the measurement is switched again to that at the measurement spot A so as to be equal to the time period $\Delta T$, i.e., the measurement spot may be switched at uniform intervals of the time period $\Delta T$.

The predetermined time period $\Delta T$ depends on a velocity of gas flow and lengths of flues which depend, in turn, on a scale of the garbage incinerator. When the lengths of the respective collecting ducts 7a, 8a extending from the sample gas collecting spots to the infrared spectroscopic gas analyzer 10 are relatively long, a quantity of still not improved exhaust gas may stagnate in these collecting ducts 7a, 8a even after the predetermined time period $\Delta T$ has elapsed. Therefore, it is necessary to exchange such stagnating exhaust gas with the improved exhaust gas before the composition-analysis is carried out. The exchange can be achieved, for example, by energizing the induced draft fan 10a for a predetermined time period to expel the quantity of exhaust gas stagnating in the collector ducts and the return ducts and thereafter by supplying the infrared spectroscopic gas analyzer 10 with the improved exhaust gas. Accordingly, it is desirable to set the time period ΔT in consideration also of a time period necessary for such forcible gas exchange.

Switching of the measuring spots at the predetermined intervals of ΔT in the manner as has been described above allows the combustion exhaust gas to be continuously composition-analyzed even when the combustion exhaust gas is being effectively improved under the action of the neutralizer supplier 13 and/or the operating condition readjuster 14. In other words, the combustion exhaust gas can be continuously monitored.

While the system according to the invention has been described hereinabove based on the specific embodiment in which the composition-analysis is alternately carried out at two measuring spots A, B, the composition-analysis at the measuring spot B is not essential since the incinerating furnace can be adequately controlled merely by the composition-analysis at the measuring spot A so as to achieve desired elimination or alleviation of the air polluting substances emitted therefrom into the atmosphere.

The controller 12 calculates, on the basis of the analytical signals obtained at the respective measuring spots A and B, a ratio between the concentration determined at the measuring spot A and the concentration determined at the measuring spot B with respect to the given constituent contained in the exhaust gas. The constituent subjected to such calculation of the concentration ratio is not limited to the air polluting substances so far as it can be easily analyzed at either measuring spot A or B and such calculation of the concentration ratio may be carried out with respect to two or more constituents. Information on the concentration ratio is applied in the form of a concentration ratio data signal to the display 15 and the printer 16 to be displayed by the display 15 and printed by the printer 16, respectively. It should be understood that, when two or more constituents are concerned, the respective concentration ratios are preferably displayed and printed separately of one another.

The calculated concentration ratio is compared to the corresponding reference value of concentration ratio registered in the controller 12. If this calculated concentration ratio is less than the reference value of concentration ratio, the alarm signal is applied from the controller 12 to the alarm 17. Upon receipt of this alarm signal, the alarm 17 provides its alarm function in a predetermined form. In the case of two or more constituents of which the respective concentration ratios must be calculated, the system may be arranged, for example, so that the alarm signal is transmitted from the controller 12 to the alarm 17 when the respective concentration ratios of more than half of these constituents are less than the corresponding reference values of concentration ratio.

The alarm function may be, for example, generation of alarm sound from an alarm buzzer or siren, or turning on/off or lighting of an alarm lamp. As for the alarm lamp, both the turn on/off and the lighting may be used, if desired. For example, there may be provided a pair of the reference concentration ratio values for one and same constituent of the exhaust gas. In this case, the alarm lamp may be adapted to be turned on/off when the calculated concentration ratio is less than the first reference value and to be put on the light when the calculated concentration ratio is less than the second reference value. These two different forms of alarm function may be advantageously used also when the concentration ratio is simultaneously calculated on a plurality of substances. In this case, the alarm lamp may be adapted to be turned on/off when the concentration ratio calculated on one of the substances is less than the corresponding reference value of concentration ratio value and to be lit when the concentration ratios calculated on more than half of the substances are less than the respective reference values of concentration ratio.

Actuation of the alarm 17 suggests that the dust collector 3 can no more fulfill its expected efficiency and immediately must be cleaned and/or part-exchanged to restore its expected dust collecting efficiency.

As will be apparent from the foregoing description, the inventive combustion system for sooty smoke generating facilities allows the sample gas of high component concentration to be directly subjected to analysis by composition-analyzing the combustion exhaust gas immediately at the outlet of the garbage incinerating furnace. In this way, composition-analysis of the combustion exhaust gas can be achieved not only easily but also in substantially continuous manner. Consequently, the analytical result can be reflected on the operating condition of the garbage incinerating furnace and thereby the air polluting substances contained in the exhaust gas can be rapidly collected. Continuous analysis of the exhaust gas, one of the most important features of the invention, allows the quantity of neutralizer to be thrown into the furnace to be properly controlled. Thereby the cost of the neutralizer can be minimized and, in consequence, the air polluting substances contained in the exhaust gas can be collected at the correspondingly reduced cost.

According to the invention, the exhaust gas is composition-analyzed before and behind the dust collector and then the concentration ratio is calculated on one or more predetermined substance(s) so that a change in the dust collecting efficiency of the dust collector is detected on the basis of a change in the concentration ratio(s). Detection of dust collecting efficiency enables the dust collector operator to determine a proper timing, i.e., frequency for cleaning and/or part-exchanging of the dust collector. In this manner, time and labor for operation of such cleaning and/or part-exchanging can be alleviated and the cost of the parts can be also reduced.

The exhaust gas destined to be emitted into the atmosphere is composition-analyzed and thereby monitored so that the air polluting substances may be effectively collected before they are emitted into the atmosphere.

As another important feature of the invention, the analyzer is operatively associated with two ducts and respective ends of these two ducts opposite to those communicating with the analyzer are connected to the exhaust gas duct at different spots. Such arrangement allows the exhaust gas to be analyzed by the single analyzer at the outlet of the combustion furnace and the spot immediately before which the exhaust gas is emitted into the atmosphere, i.e., before and behind the dust collector. In addition, the measuring spots are switched from one to another at the predetermined intervals and thereby the exhaust gas can be continuously composition-analyzed at either measuring spot.

Furthermore, actuation of the alarm allows the operator to determine the proper timing for cleaning and/or part-exchanging of the dust collector without relying upon the printed data of the variation occurring in the concentration ratio.

Use of the infrared spectroscopic gas analyzer as the analyzer allows the operator to measure not only the air polluting substances but also the other various substances in order to determine the currently available dust collecting efficiency so far as the other various substances are suitable for calculation of the concentration ratio. Moreover, the invention can provide the operating condition readjuster at a relatively low cost. Therefore, the combustion system according to the invention correspondingly reduce the construction cost for the garbage incinerating facilities and can be readily installed in the existing sooty smoke generating facilities.

A bag filter may be used as the dust collector to catch various substances contained in the exhaust gas as completely as possible and thereby to alleviate or eliminate the air polluting substances which otherwise might be emitted into the atmosphere.

What is claimed is:

1. A combustion system for sooty smoke generating facilities in which a post-treatment stage for combustion exhaust gas is provided closely adjacent an outlet of a combustion furnace and said combustion exhaust gas is emitted into the atmosphere after having passed through said post-treatment stage, said combustion system comprising:

a first analyzer adapted to permit introduction of the combustion exhaust gas into said first analyzer from a spot adjacent the outlet of the combustion furnace and to composition-analyze said combustion exhaust gas, a second analyzer adapted to composition-analyze the combustion exhaust gas flowing from said post-treatment stage toward a chimney stack, a controller adapted to process an analytical signal provided from said first analyzer and to output a control signal based on said analytical signal, a neutralizer supplier adapted to, upon receipt of said control signal provided from said controller, supply said combustion furnace with neutralizers of predetermined types, and an operating condition readjuster adapted to, upon receipt of said control signal provided from said controller, change at least one of combustion temperature and combustion time period of the combustion furnace and turbulence condition during combustion so as to readjust the operating condition of said combustion furnace, wherein, based on said control signal, said neutralizer supplier supplies said combustion furnace with said neutralizers by quantities sufficient to neutralize the quantities of respective components contained in said combustion exhaust gas and said operating condition readjuster controllably readjusts the operating condition of said combustion furnace, and wherein said second analyzer monitors the composition of the combustion exhaust gas to be emitted into the atmosphere.

2. A combustion system for sooty smoke generating facilities in which a post-treatment stage for combustion exhaust gas is provided closely adjacent an outlet of a combustion furnace and said combustion exhaust gas is emitted into the atmosphere after having passed through said post-treatment stage, said combustion system comprising:

an analyzer adapted to composition-analyze said combustion exhaust gas, a controller adapted to process an analytical signal provided from said analyzer and to output a control signal based on said analytical signal, a neutralizer supplier adapted to, upon receipt of said control signal provided from said controller, supply said combustion furnace with neutralizers of predetermined types, an operating condition readjuster adapted to, upon receipt of said control signal provided from said controller, change at least one of combustion temperature and combustion time period of said combustion furnace and turbulence condition during combustion so as to controllably readjust the operating condition of said combustion furnace, a first duct through which the combustion exhaust gas is introduced from a spot adjacent the outlet of the combustion furnace into said analyzer, a second duct through which the combustion exhaust gas flowing from said post-treatment stage toward a chimney stack is introduced into said analyzer, and a duct switcher serving to switch in flow path for the exhaust gas between said first and second ducts at predetermined time intervals, wherein, based on said control signal depending on an analytical result of the combustion exhaust gas introduced through said first duct, said neutralizer supplier supplies said combustion furnace with said neutralizers by quantities sufficient to neutralize the quantities of components contained in said combustion exhaust gas, on one hand, and said operating condition readjuster controllably readjusts the operating condition of said combustion furnace, on the other hand, and wherein the composition of said combustion exhaust gas to be emitted into the atmosphere is monitored on the basis of the analytical result of said combustion exhaust gas introduced through said second duct.

3. A combustion system for sooty smoke generating facilities in which a post-treatment stage for combustion exhaust gas is provided closely adjacent an outlet of a combustion furnace and said combustion exhaust gas is emitted into the atmosphere after having passed through said post-treatment stage, said combustion system comprising:

a dust collector provided in said post-treatment stage for combustion exhaust gas to collect predetermined substances contained in the exhaust gas generated from said combustion furnace, a first analyzer adapted to permit introduction of the exhaust gas into said first analyzer from a flue extending between said combustion furnace and said dust collector and to composition-analyze said exhaust gas, a second analyzer adapted to be supplied with the exhaust gas from a flue extending between said dust collector and an outlet immediately into the atmosphere and to composition-analyze said exhaust gas, and a controller adapted to be applied with analytical signals from said first analyzer and second analyzer, respectively, wherein said controller calculates a ratio between a concentration of a given substance determined by said first analyzer and a concentration of this substance determined by said second analyzer and measures a dust collecting efficiency of said dust collector on the basis of this concentration ratio.

4. A combustion system for sooty smoke generating facilities in which a post-treatment stage for combustion exhaust gas is provided closely adjacent an outlet of said combustion furnace and said combustion exhaust gas is emitted into the atmosphere after having passed through said post-treatment stage, said combustion system comprising:

a dust collector provided in said post-treatment stage for combustion exhaust gas to collect predetermined substances contained in said exhaust gas generated from said combustion furnace, a first analyzer adapted to permit introduction of the exhaust gas into said first analyzer from a flue extending between said combustion furnace and said dust collector and to composition-analyze said exhaust gas, a second analyzer adapted to be supplied with the exhaust gas from a flue extending between said dust collector and an outlet immediately into the atmosphere, a controller adapted to be applied with analytical signals from said first analyzer and second analyzer, respectively, a neutralizer supplier adapted to, upon receipt of an operation control signal provided by said controller as a result of processing said analytical signal from said first analyzer, supply said combustion furnace with neutralizers of predetermined types, and an operating condition readjuster adapted to, upon receipt of said operation control signal, change at least one of combustion temperature and combustion time period of said combustion furnace and turbulence condition during combustion so as to readjust the operating condition of said combustion furnace, wherein said controller calculates a ratio between a concentration of a given substance determined by said first analyzer and a concentration of this substance determined by said second analyzer and measures a dust collecting efficiency of said dust collector on the basis of said concentration ratio, and wherein, based on said operation control signal, said neutralizer supplier supplies the combustion furnace with the neutralizers by quantities sufficient to neutralize the quantities of respective components contained in the exhaust gas and said operating condition readjuster controllably readjusts the operating condition of said combustion furnace.

5. A combustion system for sooty smoke generating facilities in which a post-treatment stage for combustion exhaust gas is provided closely adjacent an outlet of a combustion furnace and combustion exhaust gas is emitted into the atmosphere after having passed through said post-treatment stage, said combustion system comprising:

a dust collector provided in said post-treatment stage for combustion exhaust gas to collect predetermined substances contained in the exhaust gas generated from said combustion furnace, an analyzer adapted to composition-analyze said exhaust gas, a controller adapted to process an analytical signal provided from said analyzer, a first duct through which the exhaust gas is introduced into said analyzer from a flue extending between said combustion furnace and said dust collector, a second duct through which the exhaust gas is introduced into said analyzer from a flue extending between said dust collector and an outlet immediately into the atmosphere, and a duct-switcher adapted to switch the flow path for the exhaust gas between said first and second ducts at predetermined time intervals, wherein said controller calculates a ratio between a concentration of a given substance contained in the exhaust gas introduced through said first duct and a concentration of this substance contained in the exhaust gas introduced through said second duct and measures a dust collecting efficiency of said dust collector on the basis of said concentration ratio.

6. A combustion system for sooty smoke generating facilities in which a post-treatment stage for combustion exhaust gas is provided closely adjacent an outlet of a combustion furnace and combustion exhaust gas is emitted into the atmosphere after having passed through said post-treatment stage, said combustion system comprising:

a dust collector provided in said post-treatment stage of the combustion furnace to collect predetermined substances contained in the exhaust gas generated from said combustion furnace, an analyzer adapted to composition-analyze said exhaust gas, a controller adapted to process an analytical signal provided from said analyzer, a first duct through which the exhaust gas is introduced into said analyzer from a flue extending between said combustion furnace and said dust collector, a second duct through which the exhaust gas is introduced into said analyzer from a flue extending between said dust collector and an outlet immediately into the atmosphere, a duct-switcher adapted to switch the flow path for the exhaust gas between said first and second ducts at predetermined time intervals, a neutralizer supplier adapted to, upon receipt of an operation control signal provided by said controller as a result of processing said analytical signal from said analyzer depending on the combustion exhaust gas introduced through said first duct, supply said combustion furnace with neutralizers of predetermined types, and an operating condition readjuster adapted to, upon receipt of said operation control signal, change at least one of combustion temperature and combustion time period of said combustion furnace and turbulence condition during combustion so as to readjust the operating condition of said combustion furnace, wherein said controller calculates a ratio between a concentration of a given substance contained in the exhaust gas introduced through said first duct and a concentration of this substance contained in the exhaust gas introduced through said second duct and measures a dust collecting efficiency of said dust collector on the basis of this concentration ratio, and wherein, based on said operation control signal, said neutralizer supplier supplies said combustion furnace with the neutralizers by quantities sufficient to neutralize the quantities of respective components contained in the exhaust gas and said operating condition readjuster controllably readjusts the operating condition of said combustion furnace.

7. The combustion system for sooty smoke generating facilities according to any one of claims 3 through 6, wherein said dust collector is provided in the form of a bag filter.

8. The combustion system for sooty smoke generating facilities according to claim 7, comprising:

an alarm adapted to be actuated upon receipt of an alarm signal provided from said controller, and said controller providing said alarm signal when the concentration ratios calculated by said controller fall below the respective predetermined values.

9. The combustion system for sooty smoke generating facilities according to claim 7, wherein an analyzer employed in said combustion system for sooty smoke generating facilities is provided in the form of a measuring instrument for precursors of dioxins such as chlorophenol, chlorobenzene or PCB (polychlorinated biphenyl).

10. The combustion system for sooty smoke generating facilities according to claim 3 or 4, wherein a composition of the combustion exhaust gas being emitted into the atmosphere is monitored on the basis of concentrations of the predetermined substances determined by said second analyzer.

11. The combustion system for sooty smoke generating facilities according to claim 10, comprising:
   an alarm adapted to be actuated upon receipt of an alarm signal provided from said controller, and
   said controller providing said alarm signal when the concentration ratios calculated by said controller fall below the respective predetermined values.

12. The combustion system for sooty smoke generating facilities according to claim 10, wherein an analyzer employed in said combustion system for sooty smoke generating facilities is provided in the form of a measuring instrument for CO or $O_2$.

13. The combustion system for sooty smoke generating facilities according to claim 10, wherein an analyzer employed in said combustion system for sooty smoke generating facilities is provided in the form of a measuring instrument for precursors of dioxins such as chlorophenol, chlorobenzene or PCB (polychlorinated biphenyl).

14. The combustion system for sooty smoke generating facilities according to claim 5 or 6, wherein a composition of the combustion exhaust gas being emitted into the atmosphere is monitored on the basis of concentrations of the predetermined substances contained in the exhaust gas introduced into said analyzer through said second duct and determined by said analyzer.

15. The combustion system for sooty smoke generating facilities according to claim 14, comprising:
   an alarm adapted to be actuated upon receipt of an alarm signal provided from said controller, and
   said controller providing said alarm signal when the concentration ratios calculated by said controller fall below the respective predetermined values.

16. The combustion system for sooty smoke generating facilities according to claim 14, wherein an analyzer employed in said combustion system for sooty smoke generating facilities is provided in the form of a measuring instrument for CO or $O_2$.

17. The combustion system for sooty smoke generating facilities according to claim 14, wherein an analyzer employed in said combustion system for sooty smoke generating facilities is provided in the form of a measuring instrument for CO or $O_2$.

18. The combustion system for sooty smoke generating facilities according to claim 14, wherein an analyzer employed in said combustion system for sooty smoke generating facilities is provided in the form of a measuring instrument for precursors of dioxins such as chlorophenol, chlorobenzene or PCB (polychiorinated biphenyl).

19. The combustion system for sooty smoke generating facilities according to any one of claims 3 through 6, further comprising:
   an alarm adapted to be actuated upon receipt of an alarm signal provided from said controller, and
   said controller providing said alarm signal when the concentration ratios calculated by said controller fall below the respective predetermined values.

20. The combustion system for sooty smoke generating facilities according to claim 19, wherein an analyzer employed in said combustion system for sooty smoke generating facilities is provided in the form of a measuring instrument for CO or $O_2$.

21. The combustion system for sooty smoke generating facilities according to claim 19, wherein an analyzer employed in said combustion system for sooty smoke generating facilities is provided in the form of a measuring instrument for precursors of dioxins such as chlorophenol, chlorobenzene or PCB (polychlorinated biphenyl).

22. The combustion system for sooty smoke generating facilities according to claim 6, wherein said analyzer is provided in the form of a measuring instrument for CO or $O_2$.

23. The combustion system for sooty smoke generating facilities according to claim 6, wherein said analyzer is provided in the form of a measuring instrument for precursors of dioxins such as chlorophenol, chlorobenzene or PCB (polychlorinated biphenyl).

24. A combustion system for sooty smoke generating facilities in which a post-treatment stage for combustion exhaust gas is provided closely adjacent an outlet of a combustion furnace and the post-treatment combustion exhaust gas is emitted into the atmosphere after having passed through said post-treatment stage, said combustion system comprising:
   an infrared spectroscopic analyzer adapted to composition-analyze the post-treatment combustion exhaust gas introduced from said combustion furnace into said infrared spectroscopic analyzer so that a composition of the combustion exhaust gas may be continuously monitored.

25. A combustion system for sooty smoke generating facilities in which a post-treatment stage for combustion exhaust gas is provided closely adjacent an outlet of a combustion furnace and the combustion exhaust gas is emitted into the atmosphere after having passed through said post-treatment stage, said combustion system comprising:
   a bag filter provided in said post-treatment stage for the combustion furnace to collect substances contained in the combustion exhaust gas generated from said combustion furnace, and
   an infrared spectroscopic analyzer adapted to composition-analyze said combustion exhaust gas introduced from said combustion furnace,
   wherein a composition of said combustion exhaust gas is continuously monitored by said infrared spectroscopic analyzer.

26. The combustion system for sooty smoke generating facilities according to claim 25, wherein the combustion exhaust gas is introduced into said infrared spectroscopic analyzer before said combustion exhaust gas passes through said bag filter.

27. The combustion system for sooty smoke generating facilities according to claim 25, wherein the combustion exhaust gas is introduced into said infrared spectroscopic analyzer after said combustion exhaust gas has passed through said bag filter.

* * * * *